(12) United States Patent
Ohnmacht et al.

(10) Patent No.: US 10,335,208 B2
(45) Date of Patent: Jul. 2, 2019

(54) DEVICE FOR CARRYING OUT A DISTRACTION OR A COMPRESSION OF VERTEBRAL BODIES DURING SPINAL SURGERY

(71) Applicant: SILONY MEDICAL INTERNATIONAL AG, Frauenfeld (CH)

(72) Inventors: Timo Ohnmacht, Trichtingen (DE); Frank Heuer, Filderstadt (DE)

(73) Assignee: SILONY MEDICAL INTERNATIONAL AG, Frauenfeld (CH)

( * ) Notice: Subject to any disclaimer, the term of this patent is extended or adjusted under 35 U.S.C. 154(b) by 43 days.

(21) Appl. No.: 15/740,602

(22) PCT Filed: Apr. 22, 2016

(86) PCT No.: PCT/EP2016/059063
§ 371 (c)(1),
(2) Date: Dec. 28, 2017

(87) PCT Pub. No.: WO2017/001080
PCT Pub. Date: Jan. 5, 2017

(65) Prior Publication Data
US 2018/0185067 A1    Jul. 5, 2018

(30) Foreign Application Priority Data

Jun. 29, 2015   (DE) .................. 10 2015 212 050

(51) Int. Cl.
*A61B 17/70*         (2006.01)
(52) U.S. Cl.
CPC ........ *A61B 17/708* (2013.01); *A61B 17/7076* (2013.01); *A61B 17/7077* (2013.01); *A61B 17/7079* (2013.01); *A61B 17/7002* (2013.01)

(58) Field of Classification Search
CPC .......................................... A61B 17/7077–708
(Continued)

(56) References Cited

U.S. PATENT DOCUMENTS

| 2012/0316609 A1* | 12/2012 | Wall ................... A61B 17/7079 606/86 A |
| 2014/0039557 A1* | 2/2014 | Stad ..................... A61B 17/708 606/279 |

(Continued)

FOREIGN PATENT DOCUMENTS

| DE | 8712943 U1 | 11/1987 |
| EP | 2305154 A1 | 4/2011 |

OTHER PUBLICATIONS

International Search Report and Written Opinion PCT/ISA/210 and PCT/ISA/237, International Application No. PCT/EP/2016/059063, pp. 1-10, International Filing Date Apr. 22, 2016, dated Jul. 5, 2016.

*Primary Examiner* — Nicholas J Plionis
(74) *Attorney, Agent, or Firm* — Bond Schoeneck & King, PLLC; George McGuire (57) ABSTRACT

Disclosed is a device for carrying out a distraction and/or a compression of vertebral bodies during spinal surgery, said device comprising a first and a second sleeve-shaped extension part, each part having a longitudinal direction and each of which parts can be secured on a bone anchor in a detachable but rigid and rotationally fixed manner. The device is characterized by a first eccentric bearing part and a second counter bearing part, which parts can be positioned on the first and on the second extension part respectively in corresponding positions, and in that, at least the eccentric bearing part can be rotated relative to the first extension part about the longitudinal direction of said extension part, such that due to the eccentricity, the first bearing part can be brought into contact with the second counter bearing part (Continued)

and thus a bearing position is formed for forming a pivot joint between the two extension parts in order to perform the distraction or compression.

20 Claims, 5 Drawing Sheets

(58) Field of Classification Search
USPC .......................................... 606/86 A, 90, 105
See application file for complete search history.

(56) References Cited

U.S. PATENT DOCUMENTS

| | | | |
|---|---|---|---|
| 2014/0027715 A1 | 9/2014 | Fowler et al. | |
| 2014/0277151 A1* | 9/2014 | Fowler ............... | A61B 17/7074 606/265 |
| 2015/0164569 A1* | 6/2015 | Reitblat ............. | A61B 17/7077 606/279 |
| 2015/0374354 A1* | 12/2015 | Boyd ................. | A61B 17/1757 600/204 |
| 2017/0020583 A1* | 1/2017 | Tsai ................... | A61B 17/7032 |
| 2017/0311995 A1* | 11/2017 | Wall ................... | A61B 17/7076 |

* cited by examiner

DEVICE FOR CARRYING OUT A DISTRACTION OR A COMPRESSION OF VERTEBRAL BODIES DURING SPINAL SURGERY

CROSS-REFERENCE TO RELATED APPLICATIONS

This application is the United States National Stage entry under 35 U.S.C. 371 of PCT/EP2016/059063 filed on Apr. 22, 2016, which claims priority to German Application No. 102015212050.3, filed Jun. 29, 2015, the entire disclosure of each of which is incorporated herein by reference.

BACKGROUND OF THE INVENTION

The invention relates to a device for carrying out a distraction or a compression of vertebral bodies during in particular minimally invasive spinal surgery, said device comprising a first and a second extension part, which parts are in particular sleeve-shaped, at least in portions, each part having a longitudinal direction and each of which parts can be secured on a bone anchor in a detachable but rigid and rotationally fixed manner, the bone anchors in each case being intended to be inserted or being already inserted into one of the vertebral bodies to be treated.

In modern spinal surgery, in particular in minimally invasive spinal surgery where sleeve-shaped extension parts of the bone anchors, referred to as extenders, are used, the problem is often that usually adjacent vertebral bodies have to be moved away from one another (distraction) or moved towards one another (compression). The new position can then be fixed by means of osteosynthesis devices, using correction rods. There are instruments for this purpose in the prior art which are sometimes designed in a complex manner and which connect the two extension parts, which parts are rigidly connected to the bone anchors inserted into the vertebral bodies, so as to be adjustable relative to one another. The known devices are complex to produce and complicated to use.

US 2014/0039557 A1 discloses a device of the type mentioned at the outset. In this device, one of the sleeve-shaped extension parts is provided with a bearing part that can be moved in the longitudinal direction and with which the other bearing sleeve-shaped extension part can be brought into contact in order to form a bearing point. The movable bearing part can be made larger by clipping on an attachment part.

US 2014/0277151 A1 also discloses a device of the type mentioned at the outset, comprising a cup-shaped bearing part which can be placed onto one of the sleeve-shaped extension parts and can optionally be moved relative to the sleeve-shaped extension part in the longitudinal direction, which bearing part comprises U-shaped or wing-shaped attachments or arms that extend outwards in the transverse direction and with which the other sleeve-shaped extension part can be brought into contact in order to form a pivot bearing point. In order to adapt the different transverse spacings of the sleeve-shaped extension parts, different bearing parts having different transverse extents are used, or one bearing part is used, one arm of which is designed so as to be length-adjustable in the transverse direction, it being possible for a rack-like locking mechanism to be used.

Proceeding herefrom, the object of the present invention is that of providing a device of the type mentioned at the outset which is less complex in design than known devices, is easy to use and can be economically produced.

SUMMARY OF THE PRESENT INVENTION

This object is achieved by a device of the type mentioned at the outset which is characterized by a first eccentric bearing part and a second counter bearing part, which parts can be positioned or are positioned on the first and on the second extension part respectively in corresponding positions in the longitudinal direction, the first eccentric bearing part being a movable component that is in addition to the first extension part, and the second counter bearing part being a movable component that is in addition to the second extension part or being formed by the second extension part itself, and in that at least the eccentric bearing part can be rotated relative to the first extension part about the longitudinal direction of said extension part, such that due to the eccentricity, the first bearing part can be brought into contact with the second counter bearing part and thus a bearing point is formed for forming a pivot joint between the two extension parts in order to perform the distraction or compression.

It has been found according to the invention that a complex coupling and adjustment device between two adjacent extension parts can be omitted by providing, according to the invention, a first eccentric bearing part and a second counter bearing part which can in particular both preferably be placed or pushed onto the extension parts, it being possible for the first eccentric bearing part to be brought into touching contact with the counter bearing part on the other extension part by means of simple rotation relative to the extension part in question. However, as soon as touching contact of this kind is formed, this forms, according to the invention, a bearing point for forming a pivot joint between the two extension parts in order to perform the distraction or compression. The second counter bearing part could also be formed by the second extension part itself by, for example, a counter bearing point being formed on the outer surface, against which counter bearing point the first eccentric bearing part can be supported.

The eccentric bearing part is formed such that the radius or the spacing of the outer periphery thereof from the rotational axis (=longitudinal central axis or longitudinal direction of the first extension part) increases in a peripheral direction, such as when a body is mounted so as to be rotatable outside the axis of symmetry thereof. Moreover, the eccentric bearing part is designed such that a curve that is tangent to and envelops the bearing part on the outside has a radius or a spacing from the rotational axis that increases constantly in the peripheral direction, and specifically at least along a part of the outer periphery that is intended for forming a bearing point together with the counter bearing part, and without comprising arms or similar protrusions that extend in the radial direction.

It would be conceivable for each of the two bearing parts to be provided, in the case of the relevant extension part, with a specific position in the longitudinal direction for positioning. However, it is advantageous for the first eccentric bearing part and/or the second counter bearing part to be able to be positioned in the longitudinal direction of the relevant extension part in variable positions in the longitudinal direction, i.e. to be variably adjustable on the relevant extension part in the relevant longitudinal direction. In this way, the pivot point or hinge point can be selected in a variable manner in the longitudinal direction, according to the conditions. All that needs to be ensured is that the two bearing parts are positioned at a mutually corresponding height and/or position in the longitudinal direction of the extension parts in order for said bearing parts to be able to cooperate to form the bearing point. This is then selected by the surgeon, according to the conditions, during surgery. A plurality of counter bearing points could also be provided on the second extension part, in succession in the longitudinal direction, in order to cooperate with the first eccentric bearing part that can be positioned in a variable manner in the longitudinal direction.

According to a further concept of the invention, it is proposed for means that are positively arresting in the longitudinal direction to be provided between the first eccentric bearing part and the second counter bearing part, which means stabilize the bearing point and prevent the bearing parts from sliding apart in the longitudinal direction while the distraction or compression is being performed. The bearing point is stabilized as a result. Here and in the following, the wording "between the first eccentric bearing part and the second counter bearing part" is to be understood in a functional meaning, i.e. the means can be formed materially by one and/or by the other part. This is even preferred, in order that no further components need to be used.

Moreover, it is advantageous for means that are positively arresting in the peripheral direction to be provided between the first eccentric bearing part and the second counter bearing part, which means stabilize the bearing point and prevent the bearing parts from sliding apart in the peripheral direction while the distraction or compression is being performed. Preferably, the bearing point is stabilized by positively arresting means of this kind both in the longitudinal direction and in the peripheral direction, in order to securely support, against one another, the extension parts that are to be pivoted with respect to one another, and to safely guide the distraction or compression movement.

The positively arresting means mentioned can be achieved in several ways, in particular by means of additional engagement means and securing means in the form of splints, pins or the like. However, it is advantageous for the means that are positively arresting in the longitudinal direction between the first eccentric bearing part and the second counter bearing part and/or the means that are positively arresting in the peripheral direction between the first eccentric bearing part and the second counter bearing part to be formed simply by surface shaping of the first eccentric bearing part and of the second counter bearing part, i.e. without requiring further elements. A construction of this kind simplifies the use and reduces the complexity of the device.

In a further embodiment of the invention, it is advantageous for the first eccentric bearing part or the second counter bearing part to comprise a radially outwardly open groove that extends in the peripheral direction and in particular concentrically to the longitudinal direction, and for the other bearing part in each case to comprise a radially outwardly projecting region for engaging in the groove. An embodiment of this kind makes it possible to achieve positional fixing of the two bearing parts, and thus of the two extension parts, relative to one another, which fixing is positive in the longitudinal direction but is at the same time movable or pivotable. The mentioned groove and the mentioned radially outwardly projecting region thus form means that are positively arresting in the longitudinal direction. In this case, the width of the groove is preferably greater than the corresponding shape of the projecting region for engaging in the groove, and/or in any case the groove and the projecting region for engagement in the groove do not have an exactly complementary design, in order for engagement and the formation of a bearing point to be possible even if the two extension parts do not extend in the same plane but in particular extend "askew" relative to one another.

The groove is preferably formed in the second counter bearing part and preferably extends concentrically to the longitudinal direction of the associated extension part.

In a development of the invention, it is advantageous for the means that are positively arresting in the longitudinal direction and/or in the peripheral direction to be formed by the first eccentric bearing part and the second counter bearing part being in contact with one another, depending on the rotational position of the bearing parts with respect to one another, in the region of the bearing point by means of locking positions that are in succession in the peripheral direction. According to this further concept of the invention, successive discrete positions of the two bearing parts relative to one another are achieved in the peripheral direction. The term "locking position" is to be understood here in the sense of a discrete contact position of this kind of the two parts relative to one another.

According to a further concept of the invention, it is proposed for the means that are positively arresting in the longitudinal direction and/or in the peripheral direction to be formed by the first bearing part and the second counter bearing part being in contact with one another over curved or rounded surface regions in the region of the bearing point. For example, one bearing part could comprise, in the region of the bearing point, a groove extending in the peripheral direction and comprising an in particular rounded groove base, while a region on the other bearing part that projects radially outwards and engages in said groove has a shape that is approximately complementary thereto, in particular a saddle shape. Of course, other embodiments are also conceivable and possible, a merely approximately complementary design being sufficient provided that it is possible for one bearing part to engage in the other bearing part, while forming a positionally stabilized bearing point.

It is further proposed, according to the invention, for the locking position or the curved or rounded surface regions to be formed by a surface shaping of the two bearing parts, and in particular by a surface shaping of the groove on one bearing part and/or of the radially outwardly projecting region on the other bearing part for engagement in the groove.

It is furthermore proposed for the first eccentric bearing part or the second counter bearing part to be formed homogenously in the peripheral direction in the region of the contact with the other bearing part in each case, and for the other bearing part in each case to have a shape in the peripheral direction that varies but repeats. A design of the bearing point that is self-arresting at least in the peripheral direction can be achieved in this way too.

It is particularly simple, and therefore advantageous, for the first eccentric bearing part and/or the second counter bearing part to be formed as a slotted sleeve comprising in particular a substantially cylindrical inside wall. In this way, the bearing parts can be placed or pushed onto the usually sleeve-shaped extension parts.

In this case, it is advantageous for the first eccentric bearing part and/or the second counter bearing part to be able to be positioned on the relevant extension part in a clamped manner. Clamped positioning of this kind can be achieved particularly simply by an inner diameter of the relevant bearing part being selected so as to be slightly smaller than an outer diameter of the relevant extension part, the relevant bearing part then nonetheless being able to be pushed onto the relevant extension part by means of a slight widening on account of the slit. The dimensions should be selected such that the forces for placing or pushing on the relevant bearing part can easily be applied by hand, but such that a self-arresting, clamped fit of the bearing part in the axial position intended by the surgeon on the extension part can nonetheless be achieved.

Further features, details and advantages of the invention can be found in the accompanying claims and in the schematic depiction and the following description of a preferred embodiment of the invention.

DETAILED DESCRIPTION

Figure 1A:
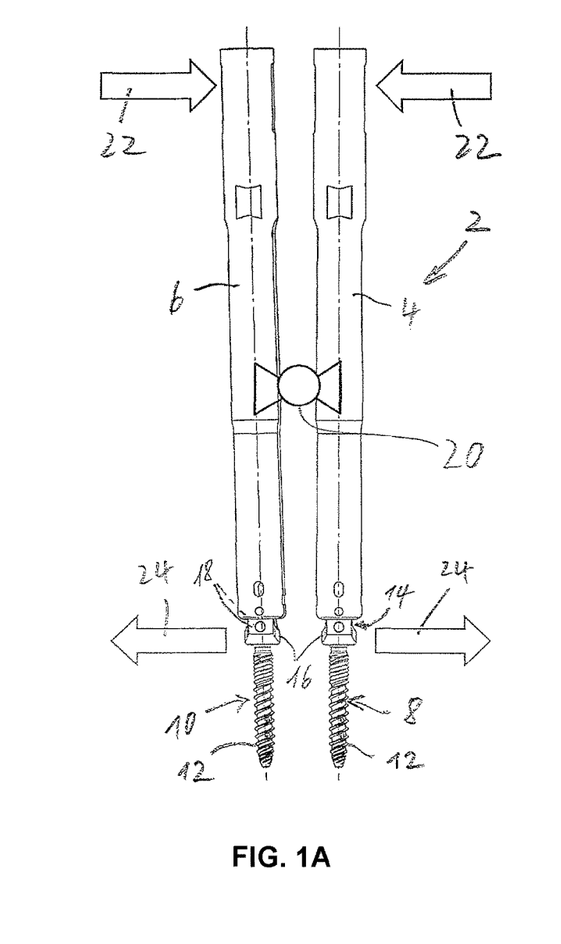
FIG. 1a is a schematic view of the conditions during a distraction of vertebral bodies during spinal surgery.
Figure 1B:
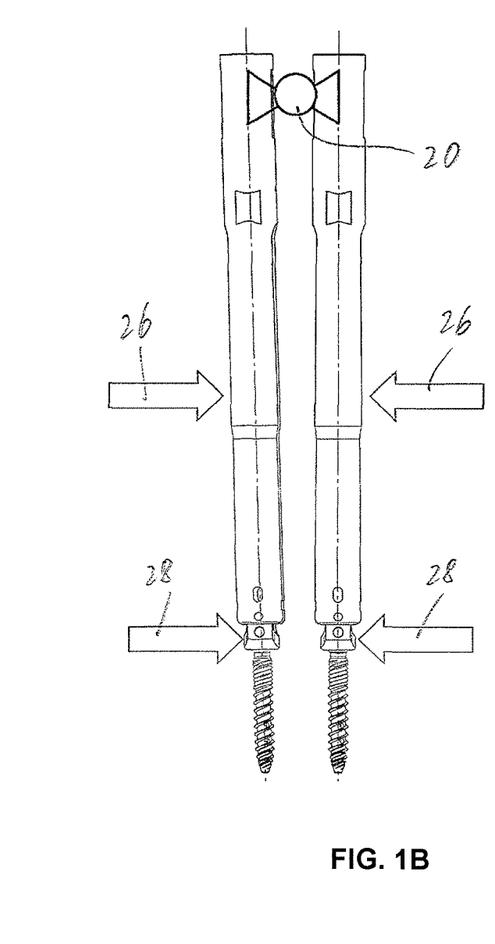
FIG. 1b is a schematic view of the conditions during a compression of vertebral bodies during spinal surgery.

FIG. 1a schematically shows the conditions during a distraction and FIG. 1b shows said conditions during a compression of vertebral bodies during spinal surgery. A device according to the invention and denoted overall by reference sign 2 is shown schematically, said device comprising a first and a second sleeve-shaped extension part 4 and 6, respectively, shown by way of example in an upper region. Each extension part 4, 6 is connected to an associated bone anchor 8 and 10, respectively, in a detachable but rigid and rotationally fixed manner. The bone anchor 8, 10 is, by way of example and preferably, an osteosynthesis device, the bone anchor 8, 10 in each case comprising a threaded shank 12 to be screwed into a vertebral body, and a clevis 16 that is U-shaped in a side view, comprises a receiving opening 14 for a correction element, in particular a correction rod, and comprises two limbs 18. In this case, the relevant screw shank 12 is either formed rigidly, in particular integrally, with the clevis 16, or in each case comprises a head that is pivotally mounted inside the clevis 16 and is permanently fixed by the surgeon in an intended pivot position relative to the clevis 16. The latter case is referred to as a polyaxial bone anchor, in particular a polyaxial bone screw. After the bone anchors 8, 10 have been inserted, in particular screwed, into usually adjacent vertebral bodies, a distraction (FIG. 1a) or a compression (FIG. 1b) of the vertebral bodies relative to one another can be performed. For this purpose, FIG. 1a schematically shows a bearing point 20 in the manner of a pivot joint between the extension parts 4 and 6. The arrows 22 shown at the top of FIG. 1a indicate an application of force and/or a pivot movement of the two extension parts 4 and 6 relative to the bearing point 20. The bone anchors 8, 10 and, together therewith the vertebral bodies, are moved slightly away from one another in accordance with the arrows 24 shown at the bottom in FIG. 1a, by means of a transmission of force and movement from the distal ends of the extension parts 4, 6 to the relevant clevis 16 of the bone anchor 8 or 10, and this is referred to as distraction. In the case of the compression shown in FIG. 1b, a bearing point 20, shown accordingly, is usually provided higher up in the proximal direction, i.e. in the direction directed away from the bone anchor, and, upon an application of force in accordance with the arrows 26, the distal ends of the extension parts 4, 6 are moved towards one another, which is indicated by the arrows 28. As a result, the bone anchors 8, 10 screwed into the vertebral bodies, and thus the vertebral bodies, are moved towards one another, and this is referred to as compression.

Figure 2:
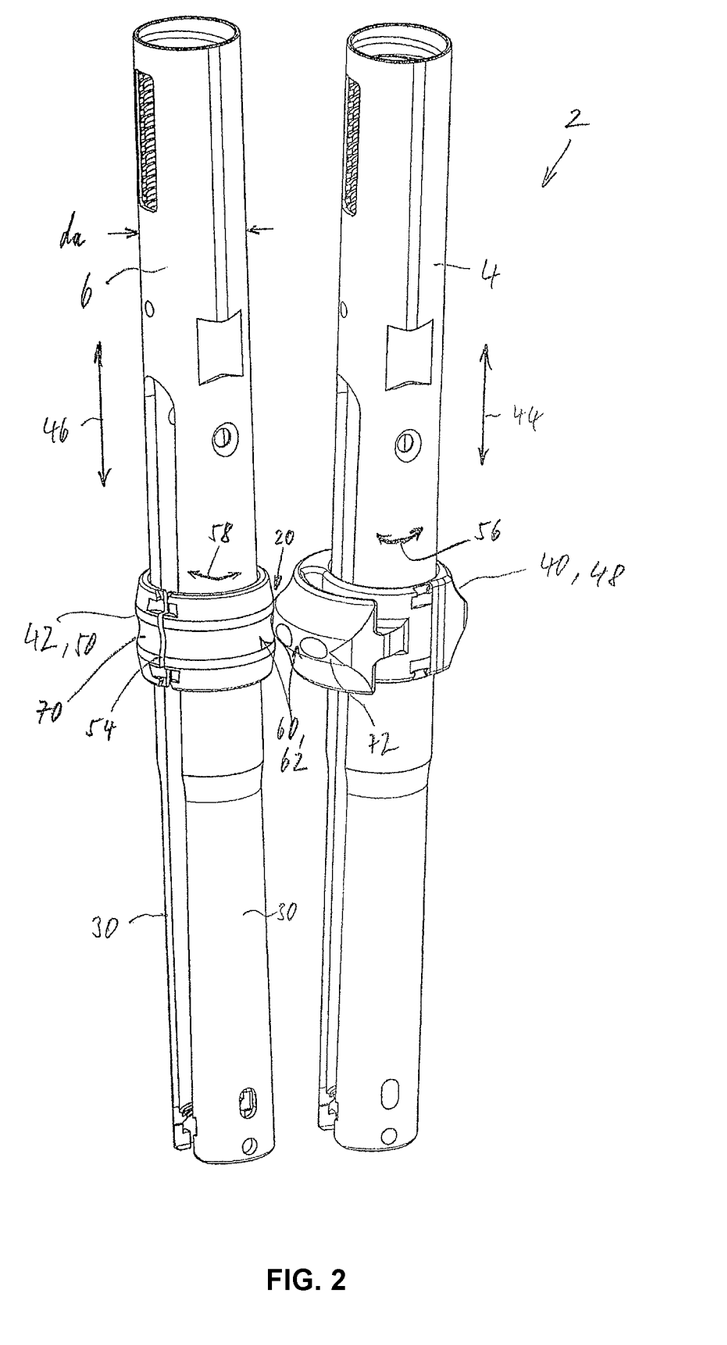
FIG. 2 is a perspective view of a device according to the invention for carrying out a distraction and/or a compression of vertebral bodies during spinal surgery, comprising two extension parts and a first eccentric bearing part and a second counter bearing part.

FIG. 2 shows a device 2 according to the invention, comprising two extension parts 4, 6. It can be seen that, in the case shown by way of example, the two extension parts 4, 6 are sleeve-shaped in an upper region and each comprise two distally tapering clamping limbs 30 that are slightly sprung against one another and by means of which said extension parts can be fixed to the limbs 18 of the clevis 16 of a bone anchor in a detachable but rigid and rotationally fixed manner. Further ordered parts that are effective inside or outside the extension parts 4, 6 can be used for the purpose of fixing. Instead of the clamping limbs 30, a rigid sleeve shape having another mechanism for fastening to the bone anchor can be used. The device 2 according to the invention further comprises a first eccentric bearing part 40 and a second counter bearing part 42. The two bearing parts 40 and 42 are placed or pushed onto the relevant extension part 4 or 6. Said bearing parts can be moved relative to the relevant extension part 4, 6 in the relevant longitudinal direction 44 or 46. Said bearing parts can be positioned in mutually corresponding positions in the longitudinal direction 44, 46 and, in the case shown by way of example, are clamped in this position.

In the case shown, the first eccentric bearing part 40 and the second counter bearing part 42 are formed as a slotted sleeve 48 and 50, respectively. A relevant slot 52 or 54 can also be seen in FIGS. 3 to 5. When the bearing parts have not been pushed on, a relevant inner diameter $d_i$ of a relevant substantially cylindrical inside wall of the bearing parts 40, 42 is very slightly smaller than an outer diameter $d_a$ of the extension parts 4, 6. However, the bearing parts 40, 42 can be widened by means of the relevant slit 52, 54, and can thus be pushed onto the extension parts 4, 6 in the axial direction 44, 46. Said bearing parts are then clamped on the extension parts 4, 6 in a relevant position or height.

Due to the eccentricity of the first eccentric bearing part 40, contact between the outer periphery of the first eccentric bearing part 40 and the second counter bearing part 42 can be achieved by rotating the first eccentric bearing part 40 in a peripheral direction 56 concentrically to the longitudinal direction 44 of the relevant extension part 4, as shown in FIG. 2. The bearing point 20 and thus the formation of a pivot joint between the two extension parts 4, 6 can be achieved as a result.

It can be seen on the outer periphery of the bearing parts 40, 42 that means 60 that are positively arresting in the longitudinal direction 44, 46 and means 62 that are positively arresting in the peripheral direction 56 are achieved by a corresponding shape of the outer periphery of the bearing parts 40 and 42.

In the case shown by way of example, the second counter bearing part 42 comprises a radially outwardly open groove 70 that extends in the peripheral direction 56 concentrically to the longitudinal direction 42. The first eccentric bearing part 40 comprises a radially outwardly projecting bead-like region 72 that extends in the peripheral direction 56 for engagement in the groove 70. A positively acting arresting means 60 is thus achieved in the longitudinal direction 44, 46, i.e. when forces causing pivoting are applied, the two bearing parts 40 and 42 are held against one another in the longitudinal direction and the bearing point 20 is thus stabilized.

Figure 3:
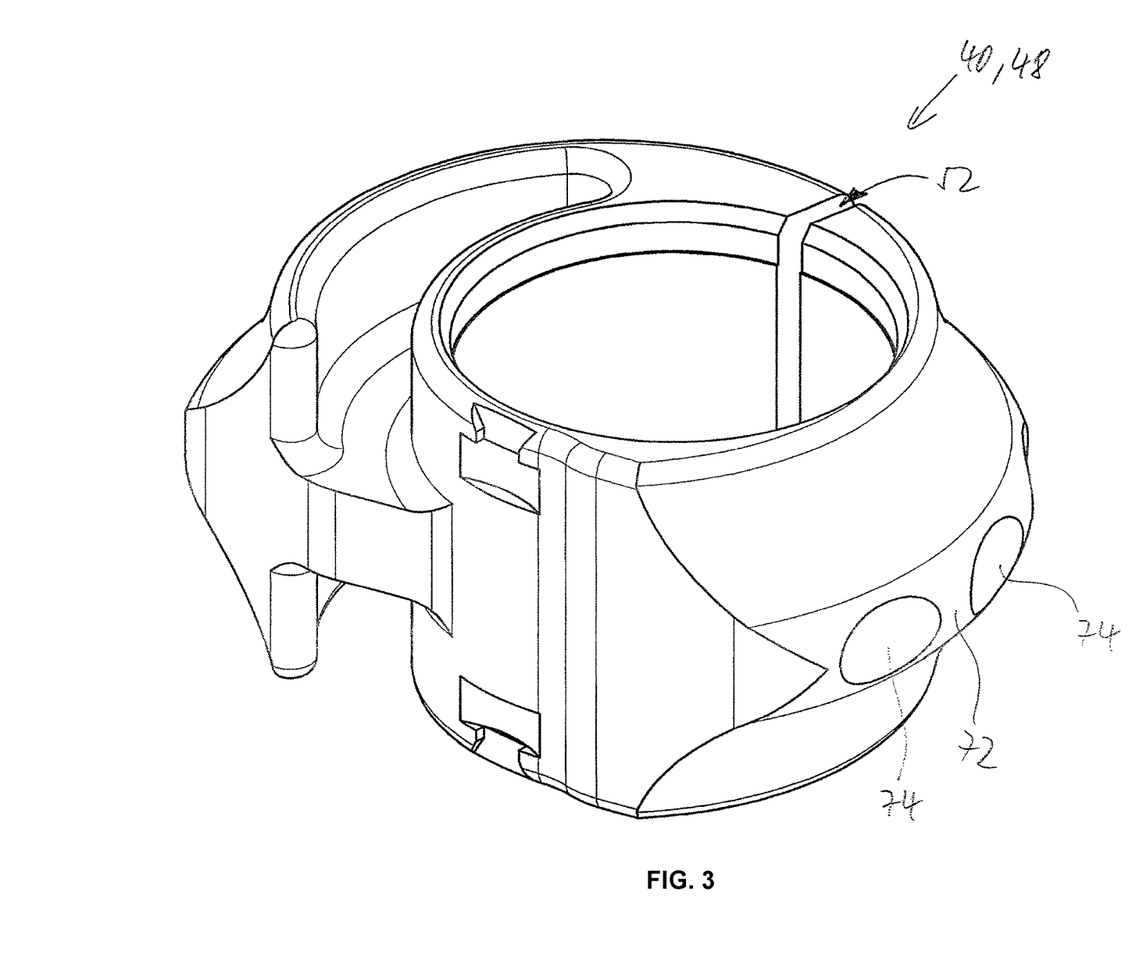
FIG. 3 is a perspective view of the first eccentric bearing part from FIG. 2.
Figure 4:
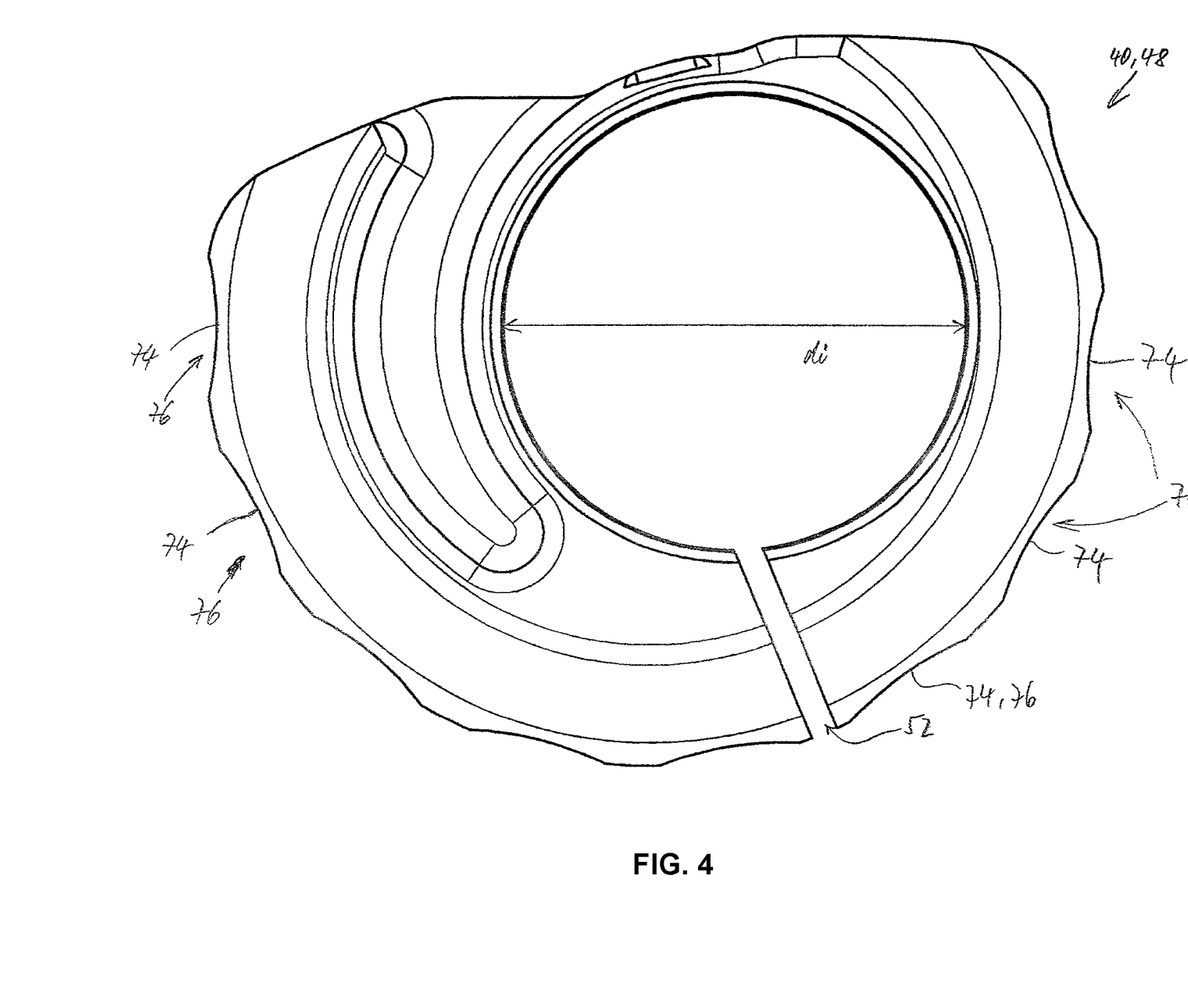
FIG. 4 is a partial view of the first eccentric bearing part according to FIG. 3, viewed in the longitudinal direction from below.
Figure 5:
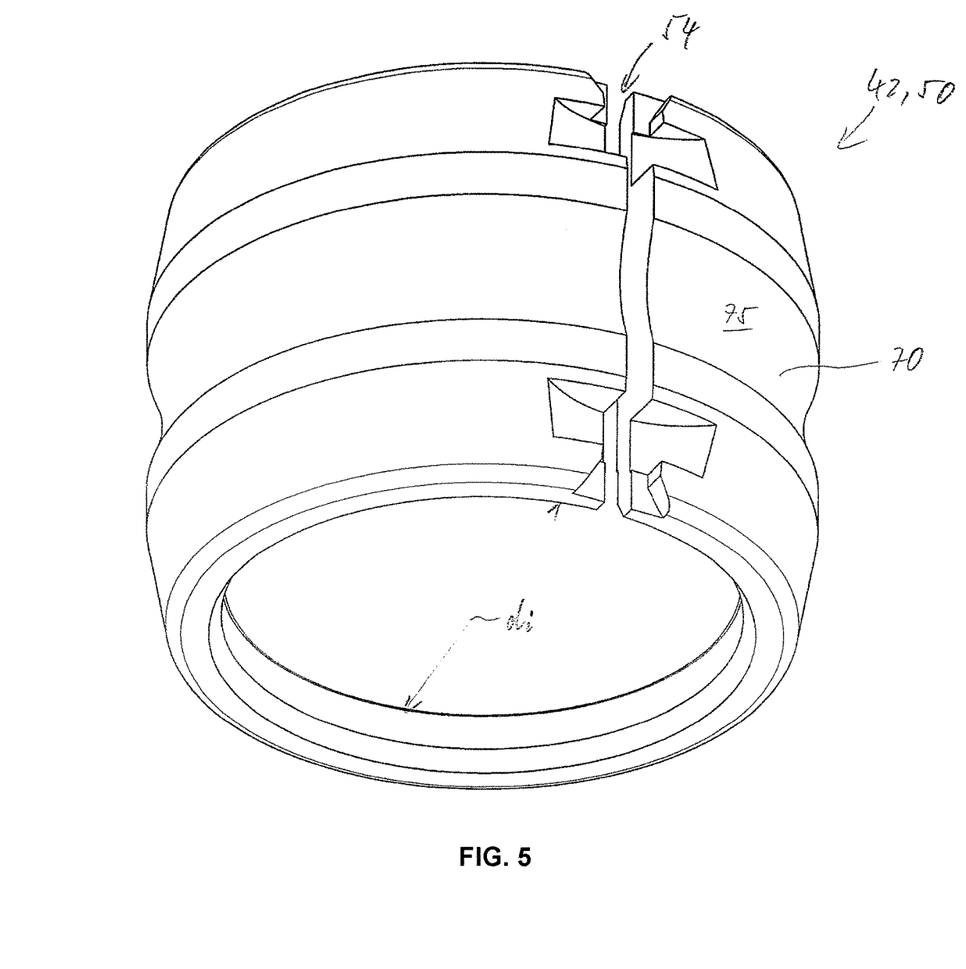
FIG. 5 is a perspective view of the second counter bearing part.

Surface regions 74 that are in succession in the peripheral direction 56 can also be seen in the bead-like region 72 of the first eccentric bearing part 40 (see FIGS. 3 and 4). Said surface regions 74 are only approximately complementary and are curved or rounded towards the surface 75 of the second counter bearing part 42 that defines the groove 70. A number of locking positions 76 that are in succession in the peripheral direction 56 are additionally formed in this way, and therefore, depending on the mutual spacing of the extension parts 4, 6, an appropriate surface region 74 can be brought into contact with the groove 70 of the second counter bearing part 42 in order to form the bearing point 20.

What is claimed is:

1. Device for carrying out at least one of a distraction and a compression of vertebral bodies during spinal surgery, said device comprising a first and a second extension part, which parts are sleeve-shaped, at least in portions, each part having a longitudinal direction and each of which parts can be secured on a bone anchor in a detachable but rigid and rotationally fixed manner, the bone anchors in each case being adapted to be either of inserted or being already inserted into one of the vertebral bodies to be treated, characterized by a first eccentric bearing part and a second counter bearing part, which parts are adapted for positioning or are positioned on the first and on the second extension part respectively in corresponding positions in the longitudinal direction, the first eccentric bearing part being a movable component that is in addition to the first extension part, and the second counter bearing part being a movable component that is either of in addition to the second extension part or being formed by the second extension part itself, and in that at least the eccentric bearing part can be rotated relative to the first extension part about the longitudinal direction of said extension part, such that due to the eccentricity, the first bearing part can be brought into contact with the second counter bearing part and thus a bearing point is formed for forming a pivot joint between the two extension parts in order to perform the distraction or compression.

2. Device according to claim 1, characterized in that, in the longitudinal direction of the relevant extension part, at least one of the first eccentric bearing part and the second counter bearing part can be positioned in variable positions in the longitudinal direction.

3. Device according to claim 1, characterized in that means that are positively arresting in the longitudinal direction are provided between the first eccentric bearing part and the second counter bearing part, which means stabilize the bearing point and prevent the bearing parts from sliding apart in the longitudinal direction while the distraction or compression is being performed.

4. Device according to claim 3, characterized in that means that are positively arresting in the peripheral direction are provided between the first eccentric bearing part and the second counter bearing part, which means stabilize the bearing point and prevent the bearing parts from sliding apart in the peripheral direction (56) while the distraction or compression is being performed.

5. Device according to claim 4, characterized in that the means that are positively arresting in the longitudinal direction and the means that are positively arresting in the peripheral direction are formed simply by a surface shaping of the first eccentric bearing part and of the second counter bearing part, without requiring further elements.

6. Device according to claim 4, characterized in that the means that are positively arresting in the longitudinal direction and in the peripheral direction are formed by the first eccentric bearing part and the second counter bearing part being in contact with one another, depending on the rotational position of the bearing parts with respect to one another, in the region of the bearing point by means of locking positions that are in succession in the peripheral direction.

7. Device according to claim 6, characterized in that at least one of the locking position, the curved, and rounded surface regions is formed by either of a surface shape of the groove or of the radially outwardly projecting region for engaging in the groove.

8. Device according to claim 4, characterized in that the means that are positively arresting in the longitudinal direction and in the peripheral direction are formed by the first bearing part and the second counter bearing part being in contact with one another over curved or rounded surface regions in the region of the bearing point.

9. Device according to claim 3, characterized in that the means that are positively arresting in the longitudinal direction and that are provided between the first eccentric bearing part and the second counter bearing part are formed simply by a surface shaping of the first eccentric bearing part and of the second counter bearing part, without requiring further elements.

10. Device according to claim 3, characterized in that the means that are positively arresting in the longitudinal direction are formed by the first eccentric bearing part and the second counter bearing part being in contact with one another, depending on the rotational position of the bearing parts with respect to one another, in the region of the bearing point by means of locking positions that are in succession in the peripheral direction.

11. Device according to claim 3, characterized in that the means that are positively arresting in the longitudinal direction are formed by the first bearing part and the second counter bearing part being in contact with one another over curved or rounded surface regions in the region of the bearing point.

12. Device according to claim 1, characterized in that at least one of the first eccentric bearing part or the second counter bearing part comprises a radially outwardly open groove that extends in the peripheral direction and concentrically to the longitudinal direction, and the other bearing part in each case comprises a radially outwardly projecting region for engaging in the groove.

13. Device according to claim 1, characterized in that at least one of the first eccentric bearing part of and the second counter bearing part is formed homogenously in the peripheral direction in the region of the contact with the other bearing part in each case, and the other bearing part in each case has a shape in the peripheral direction that varies but repeats.

14. Device according to claim 1, characterized in that at least one of the first eccentric bearing part and the second counter bearing part is formed as a slotted sleeve comprising in particular a substantially cylindrical inside wall.

15. Device according to claim 1, characterized in that at least one of the first eccentric bearing part and the second counter bearing part can be positioned on the relevant extension part in a clamped manner.

16. Device according to claim 1, further comprising one bone anchor in each case for each extension part, the bone anchor comprising a shank having a head, and a clevis that is U-shaped in a side view and has a receiving opening for a correction rod, and has two limbs, the head of the shank and the clevis either being rigidly interconnected or the head of the shank being pivotally mounted on a distal end of the clevis and in this case the clevis being able to be fixed in a pivot position intended by the surgeon relative to the head of the shank that is secured in the bone.

17. Device according to claim 1, characterized in that means that are positively arresting in the peripheral direction are provided between the first eccentric bearing part and the second counter bearing part, which means stabilize the bearing point and prevent the bearing parts from sliding apart in the peripheral direction while the distraction or compression is being performed.

18. Device according to claim 17, characterized in that the means that are positively arresting in the peripheral direction and that are provided between the first eccentric bearing part and the second counter bearing part are formed simply by a surface shaping of the first eccentric bearing part and of the second counter bearing part without requiring further elements.

19. Device according to claim 17, characterized in that the means that are positively arresting in the peripheral direction are formed by the first eccentric bearing part and the second counter bearing part being in contact with one another, depending on the rotational position of the bearing parts with respect to one another, in the region of the bearing point by means of locking positions that are in succession in the peripheral direction.

20. Device according to claim 17, characterized in that the means that are positively arresting in the peripheral direction are formed by the first bearing part and the second counter bearing part being in contact with one another over curved or rounded surface regions in the region of the bearing point.

* * * * *